(12) United States Patent
Lichtenberg

(10) Patent No.: US 7,189,218 B2
(45) Date of Patent: Mar. 13, 2007

(54) NEEDLE APPARATUS WITH QUICK/SAFE RELEASE MECHANISM

(75) Inventor: Edward Lichtenberg, 2401 Pennsylvania Ave., Apt. 18B27, Philadelphia, PA (US) 19130

(73) Assignee: Edward Lichtenberg, Philadelphia, PA (US)

( * ) Notice: Subject to any disclaimer, the term of this patent is extended or adjusted under 35 U.S.C. 154(b) by 0 days.

(21) Appl. No.: 10/914,453

(22) Filed: Aug. 9, 2004

(65) Prior Publication Data

US 2005/0080385 A1  Apr. 14, 2005

Related U.S. Application Data

(60) Provisional application No. 60/578,591, filed on Jun. 10, 2004, provisional application No. 60/493,407, filed on Aug. 7, 2003.

(51) Int. Cl.
*A61M 5/00* (2006.01)

(52) U.S. Cl. ...................................... 604/187

(58) Field of Classification Search ................ 604/110, 604/187, 200, 218, 239, 240, 242, 243, 403, 604/263, 905, 272, 264, 274; 600/576, 577
See application file for complete search history.

(56) References Cited

U.S. PATENT DOCUMENTS

| | | | |
|---|---|---|---|
| 1,015,631 A | 1/1912 | Nies | |
| 2,768,198 A | 10/1956 | Marbet et al. | 260/485 |
| 3,640,278 A * | 2/1972 | Friedman | 604/192 |
| 4,841,985 A | 6/1989 | Wanamaker | 600/576 |
| 4,984,580 A * | 1/1991 | Wanamaker | 600/576 |
| 5,413,243 A | 5/1995 | Bemis et al. | 220/481 |
| 5,536,504 A | 7/1996 | Eugster et al. | 424/450 |
| 5,959,138 A | 9/1999 | Torres-Cardona et al. | 560/190 |
| 6,191,293 B1 | 2/2001 | Levy | 554/12 |
| 6,250,465 B1 | 6/2001 | Daniels et al. | 206/370 |
| 6,379,337 B1 * | 4/2002 | Mohammad M. B. B. S. | 604/195 |
| 6,659,984 B2 | 12/2003 | Maclean Crawford et al. | 604/263 |
| 6,699,217 B2 | 3/2004 | Bennett et al. | 602/110 |

OTHER PUBLICATIONS

BD Eclipse Blood Collection Needle BD Vacutainer One Use Holder 4 Pages BD Vacutainer Systems Preanalytical Solutions 2003.
Office Action dated Dec. 3, 2002 In U.S. Appl. No. 10/116,452, now abandoned.

* cited by examiner

*Primary Examiner*—Nicholas D. Lucchesi
*Assistant Examiner*—Melissa A. McCorkle
(74) *Attorney, Agent, or Firm*—Synnestvedt & Lechner LLP

(57) ABSTRACT

A needle apparatus having a quick and safe release mechanism is described. In one embodiment, the apparatus comprises a separable needle assembly and a device body. The needle assembly includes a needle, an insertion member supporting the needle, and a knob projecting from the needle assembly. The device body includes a receiver member and is configured to receive at least a portion of the insertion member inserted therein. The receiver member has at least one slot configured to receive the knob when the needle assembly is inserted inside the receiver member. In a preferred embodiment, the slot has a first slot section extending substantially axially, and a second slot section at an angle to the first slot section and extending substantially radially. Upon insertion of the needle assembly into the needle holder, the knob is pushed by the technician through the first slot section, and then rotated in the second slot section to secure the needle assembly to the needle holder. To remove the needle assembly, the knob is rotated from the second slot section to the first slot section. Once the knob is in the first slot section, the needle assembly can be easily released from the needle holder and discarded into a sharps container.

21 Claims, 3 Drawing Sheets

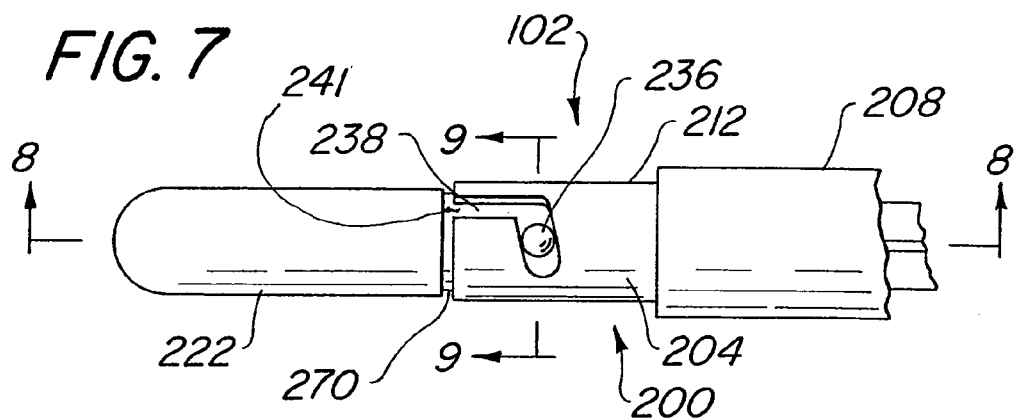
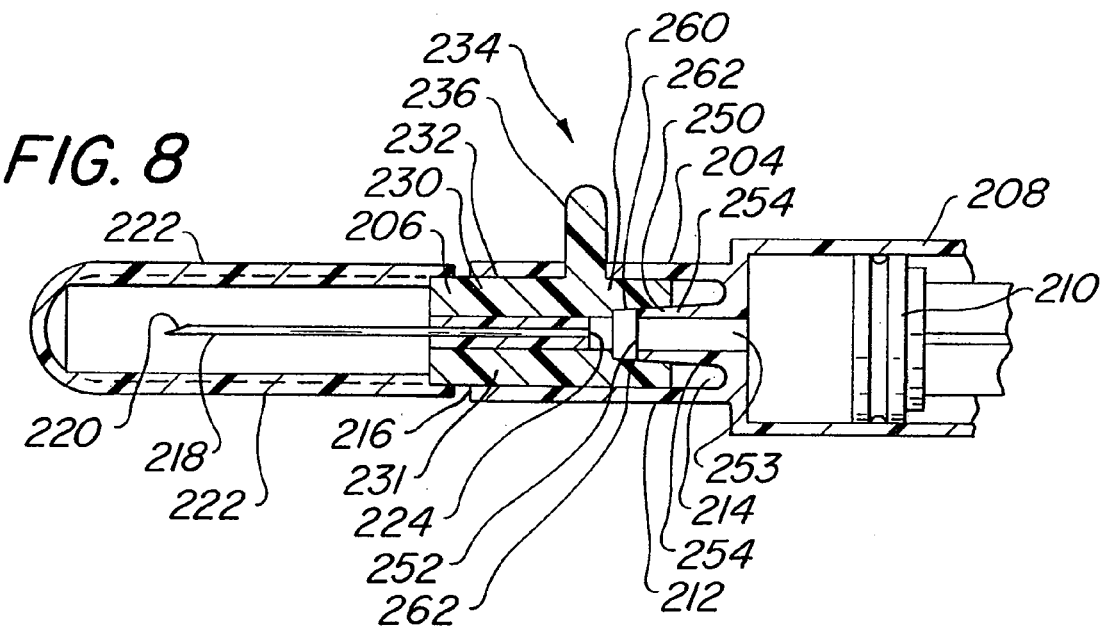
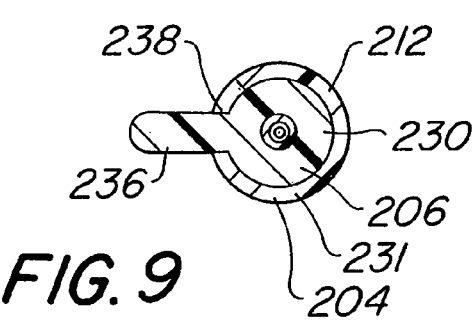
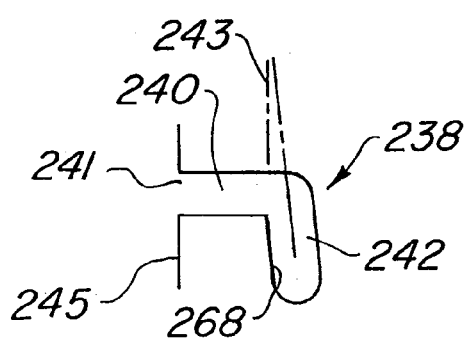

NEEDLE APPARATUS WITH QUICK/SAFE RELEASE MECHANISM

CROSS-REFERENCE TO RELATED APPLICATIONS

The present patent application claims benefit of U.S. Provisional Application Ser. Nos. 60/493,407 and 60/578,591 filed on Aug. 7, 2003, and Jun. 10, 2004, respectively. The content of the aforementioned applications are fully incorporated by reference herein.

TECHNICAL FIELD

The present invention relates generally to needle devices in which sharp needles are connected to and disconnected from needle holders, such as hypodermic needles, blood collection devices, syringes, intravenous infusion devices, fluid handling devices, and other fluid handling devices that use needles.

BACKGROUND

Handling disposable medical devices with sharp piercing needles for drawing blood and/or administering medication can be extremely risky for healthcare workers, providers, and patients. For example, any accidental needle puncture of the skin can expose a person, e.g. a healthcare worker, to pathogens such as hepatitis, HIV, or other infectious diseases, while exposing the employer, e.g., the hospital, to legal liability. Providing safe and convenient handling of such devices to reduce the risk of accidental needle sticks is a goal of most manufacturers of medical devices with needle piercing elements.

One such commonly used blood-drawing device has a double-ended needle fastened to a holder which has male threads that engage female threads at one end of an open tube. The tube holds an evacuated vial (Vacutainer™) for receiving a blood sample. One end of the hollow needle is position to puncture the Vacutainer™cap. The other end punctures a vein to draw blood. After venipuncture a Vacutainer™ is inserted into the open end of the tube, causing blood to fill the Vacutainer™. Once blood drawing is complete, the healthcare worker removes the device and sets it down to attend to the patient. The healthcare worker then disposes of the needle-tube combination in a sharps container, or unscrews the needle and disposes of it in a sharps container to reuse the Vacutainer™ tube.

This fluid collection system exposes the healthcare worker to accidental punctures of the skin by the used needle. Proximity to the used needle increases such risk, and unscrewing the needle for Vacutainer™ reuse further increases such risk. Various mechanisms and devices have been developed to improve the safety of such collection devices. Such mechanisms and devices, however, are relatively expensive. Hospitals presently prohibit tube reuse because of possible contamination. An expensive needle separation device is therefore not practical.

Another such device is a hypodermic syringe. Healthcare workers are now protected against accidental punctures of the skin from syringes in one of two ways: either the used needle is covered by a protective device, or it is retracted into the syringe body, usually by a spring-loaded release operated by the worker. In the case of covers, the technician's fingers are close to the needle, presenting a risk of an accidental stick. The cover adds to the cost of the syringe, which is another distinct disadvantage. Retractable used needles are very safe; however they are costly. In addition, when the syringe body is discarded into a sharps container, higher costs per syringe result from increased container costs and increased container disposal cost.

Accordingly, an improved cost effective device is needed to reduce the risks of accidental needle punctures of the skin.

SUMMARY

A needle apparatus having a quick and safe release mechanism is described. In one embodiment, the apparatus comprises a needle apparatus capable of collecting or dispensing fluid through a needle, for example, fluid containers and syringes. The apparatus includes a needle assembly having an insertion member and a knob projecting from the needle assembly. The needle is supported on and extends from the insertion member. The apparatus further includes a device body for holding the fluid, the body including a receiving member having an internal portion configured to receive at least a portion of the insertion member. The body has a slot configured to receive the knob when the needle assembly is inserted within the receiving member, and the knob is configured to be slideable within at least a portion of the slot when moved by a person pushing the knob within the slot. After the needle is removed from the patient, the knob is moved to a certain position within the slot. The needle assembly separates from the device body and is discarded, such as into a sharps container.

BRIEF DESCRIPTION OF THE DRAWINGS

The following detailed description will be better understood when read in conjunction with the figures appended hereto. For the purpose of illustrating the invention, there is shown in the drawings two presently preferred embodiments. It is understood, however, that this invention is not limited to these embodiments of the precise arrangements shown. It should be noted that the figures are not necessarily drawn to scale.

FIG. 7 shows a perspective view of a needle apparatus in the form of an exemplary hypodermic syringe.

FIG. 8 illustrates a cross-sectional view of the hypodermic needle taken along line 8—8 of FIG. 7.

FIG. 9 illustrates a cross-sectional view taken along line 9—9 of FIG. 7.

FIG. 10 illustrates a planar view of the slot used in the quick/safe release mechanism.

DETAILED DESCRIPTION

The present invention provides a novel needle apparatus which results in safer and lower cost needle devices. Described below are two illustrative embodiments of the present invention, one being a fluid collection device, the other being a syringe. The invention, however, is not limited to these examples.

Exemplary Fluid Collector

Figure 1:
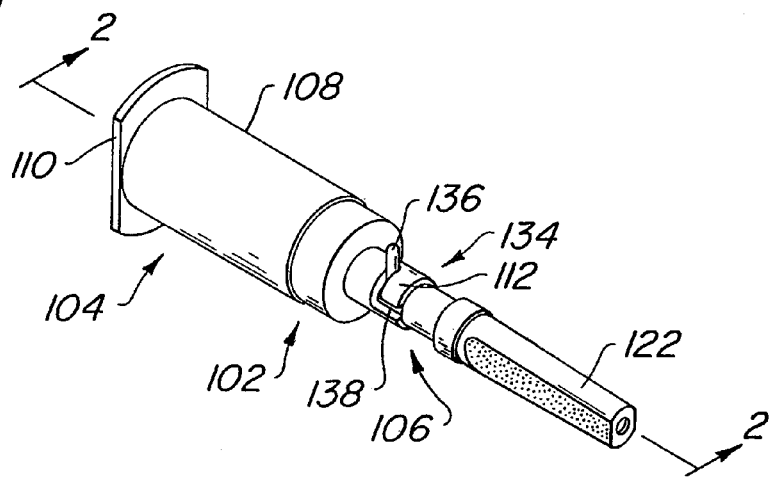
FIG. 1 illustrates a perspective view of a separable needle apparatus having a novel quick/safe release mechanism.
Figure 2:
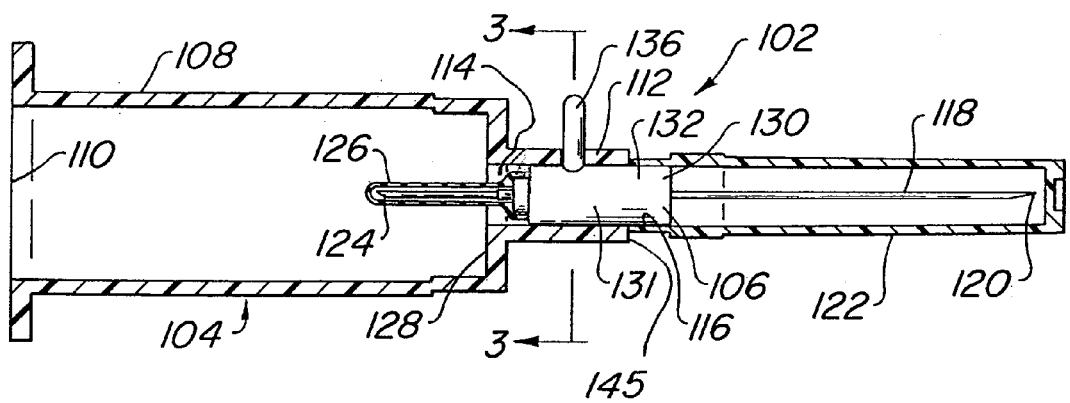
FIG. 2 illustrates a cross sectional view of the needle apparatus taken along line 2—2 of FIG. 1.

With reference to FIGS. 1, 2, 3, 4, 5, and 6, a needle apparatus 102 in the form of a fluid collection device in accordance with the present invention is now described. Such devices can include blood collection systems of the type that use a Vacutainer™. With particular reference to FIGS. 1 and 2, the needle apparatus 102 includes a device body 104 (wherein the fluid is collected), and a needle assembly 106 (which includes the needle) that is insertable into and held by the device body 104 as shown, and which is removable from the device body 104 as further described below. For orientation purposes, and with reference to FIGS. 1 and 2, the right hand side (the needle side) is the front or forward side of the device 102, and the left hand side (body side) is the back or rearward side of the device 102. This orientation shall also apply to the various elements of the device. For example, in FIG. 6, the sharp end 120 of the needle is at the front of the needle assembly 106, and the opening 116 of the receiving member is at the front of the device body 104.

The device body 104 is configured to hold the needle assembly 106 for fluid collection or delivery, and preferably forms the main body of the device. In the illustrated embodiment, the device body 104 includes a tube 108 having an open end 110 for receiving a fluid collection container, such as a Vacutainer (not shown), for collecting fluid drawn through the needle assembly 106. The tube 108 is preferably integrally formed as part of the device body 104. Alternatively, in other embodiments, as described below, the device body 104 can be a tube 108 capable of holding a fluid such as used in conjunction with a hypodermic needle or syringe (see FIGS. 7–10) or other types of fluid supply devices.

The device body 104 includes a needle receiver member 112 positioned at the front of the body 104, extending from the tube 108, and having a hollow internal portion 114 defining a frontwardly facing opening 116 at the front of the internal portion and configured to receive the needle assembly 106 therein through the opening 116. The receiver member 112 is preferably cylindrical in shape with the opening 116 generally slightly larger than and configured to receive a portion of the needle assembly 106. Having a slightly larger opening 116 enables the needle assembly 106 to fit, preferably with clearance, within device body 104 as is known in the art.

The needle assembly 106 preferably includes a longitudinally extending needle 118 having a sharp end 120 for insertion into a patient (venipuncture). A removable safety cap or cover 122 is preferably installed over the end 120 to protect against accidental sticks. Such caps are commonly used and understood by those skilled in the art. Other types of caps or shields may be used in conjunction with needle assembly 106 without departing from the inventive concepts described herein. The needle assembly 106 may also include a second or rear sharp end 124, here at an opposite end of the needle 118 from end 120 as shown, to form a double-ended hollow needle 118. The rear end 124 in this example is used to puncture the blood collection container (not shown), such as a Vacutainer™, that is inserted into the tube 108. A flexible sheath 126 covers the second sharp end 124 and is punctured by the needle end 124 when a blood collection container is inserted into the open end 110 and pushed down to a shoulder 128 of the device body 104. The operation of such needles 118 ae is known in the art.

Figure 3:
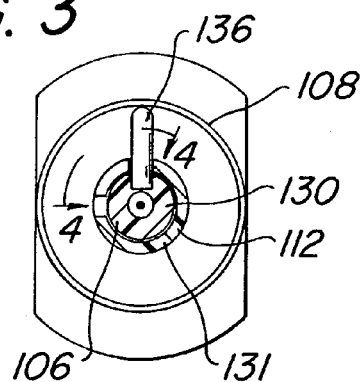
FIG. 3 illustrates a cross-sectional view taken along line 3—3 of FIG. 2.
Figure 4:
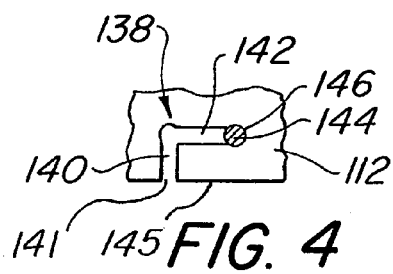
FIG. 4 illustrates a planar view of a slot within the device body.

With further reference to FIGS. 3 and 4, the needle assembly 106 includes an insert member 130, which preferably also acts as the needle holder, i.e., it supports and is connected to the needle 118, and which is configured to be inserted into the receiver member 112 of the device body 104. In the present embodiment, the insert member 130 is preferably cylindrical, formed as a collar 131 fastened to the needle 118 as shown, and preferably is coaxial to the needle 118. At least a portion of an exterior surface 132 of the 131 (insert member 130) fits within the receiver member 112.

Having introduced most of the primary components of the needle apparatus 102, it is now possible to describe the novel quick/safe release mechanism 134 in more detail.

With reference to FIGS. 1, 2, 3, 4 and 5, the novel quick/safe release mechanism 134 preferably has two primary elements, a knob 136 and a slot 138. In the preferred embodiment, the knob 136 is formed integrally as part of the needle assembly 106 for movement therewith. The slot 138 is preferably formed as part of the receiver member 112 of the device body 104. The knob 136 fits within the slot 138 when the needle assembly 106 is inserted inside the receiver member 112. The combination of the knob 136 and the slot. 138 enable the device body 104 and needle assembly 106 to attach and release from each other as desired.

In one embodiment, the knob 136 is preferably a cylindrically shaped male member in the form of a post that projects a sufficient distance to allow the technician to engage the knob 136 with his or her thumb. The knob 136 is preferably substantially perpendicular to the insert member 130 and needle 118. The knob 136 may be constricted of various materials, such as metal, composite, plastic, and other suitable materials. The knob 136 is preferably integral with insert member 130.

In one embodiment, the knob 136 may extend from the insert member 130 about a quarter of an inch, other dimensions being suitable. Additionally, the knob 136 may be formed in other shapes. In other embodiments, the knob 136 may also project radially away from the insertion member 130 at various angles that are not necessarily perpendicular to the longitudinal axis of the insertion member 130.

FIG. 4 illustrates a planar view of the slot 138 which is preferably formed as a channel within the device body 104. The slot 138 is configured to receive the knob 136 through a slot opening 141 in the front end 145 of the receiver member 112 when the needle assembly 106 is inserted inside the device body 104. In one embodiment, the slot 138 is preferably a generally L-shaped channel located in the receiving member 112 and includes a first longitudinal axial section 140, and a second radial section 142. The slot may also include a third or locking section 144.

The axial section 140 is substantially "longitudinal" or "axial," as this section is generally aligned with the axial or longitudinal direction of the needle apparatus 102 and allows the knob 136 to move with clearance in the longitudinal/axial direction when slid into or out of the slot 138. The axial section 140 is generally wider than a diameter width of the knob 136 to allow easy movement of the knob 136 in the slot 138 when inserting or removing the needle assembly 106 in the device body 104, and preferably is wide enough to allow the needle assembly 106 to fall freely from the body 102 for disposal of the needle assembly as further described below.

Located at a pivot angle from the axial section 140 is the radial section 142, which is "radial" as this section is generally aligned with the radial direction of the needle apparatus 102 and allows the knob 136 to move in a substantially radial direction when slid into or out of the slot 138. The radial section 142 need not be perfectly radial relative to the axial section 140, but simply have enough of an angle as compared to the axial section 140 such that the knob 136 will not slide or pull out of the slot 138 unless moved by the technician into the axial slot section 140. In the present embodiment, the radial slot section 142 preferably includes a width that makes the knob 136 a tight fit so that the knob 136 requires some torque to move the knob therein (an interference fit of about 0.007 inches is believed suitable). This tight fit also secures the knob 136, and thus the needle assembly to the body 102, and keeps it from sliding.

The optional locking section 144 is configured to provide an indication to the technician that the needle assembly is attached and ready for use. In the present embodiment the locking section 144 preferably includes an engagement area 146 configured to secure the knob 136. In the preferred embodiment, the engagement area 146 has a slotted shape that is generally identical to the diameter of knob 136. That is, engagement area 146 is slightly wider than the radial section 142. Accordingly, when the knob 136 is pushed through the radial section 142 and reaches the engagement area 146, the knob 36 "snaps" or "clicks" securely into place. This snapping effect indicates to the technician that the needle assembly is in its proper position Once the knob 136 engages the locking section 144, the needle apparatus 102 is ready for its intended use, such as for drawing blood.

Figure 5:
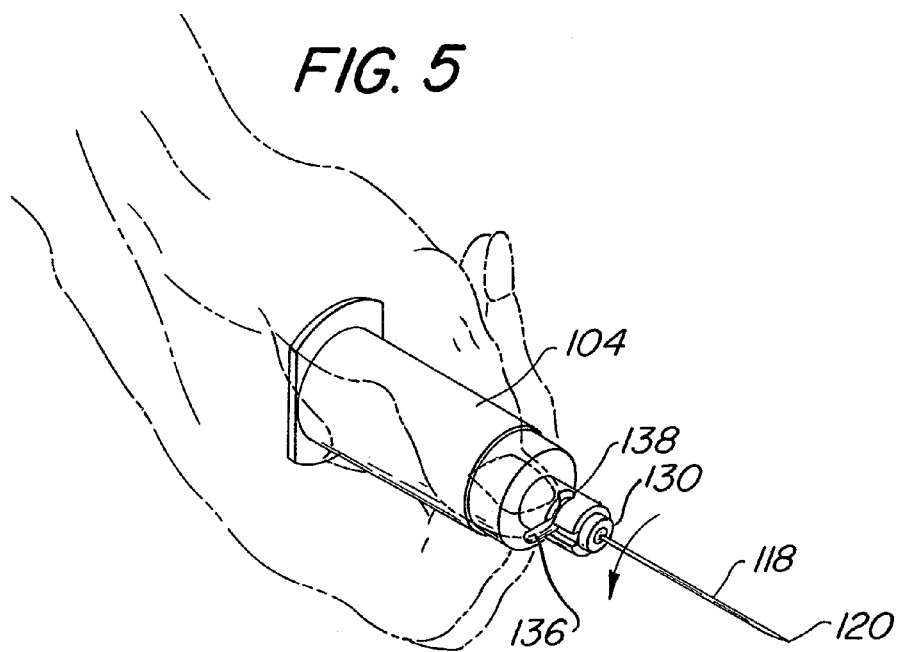
FIGS. 5 and 6 illustrate a perspective view of a needle apparatus when the needle assembly is removed from the device body, such as after completion of blood collection, the needle apparatus being held in a hand.
Figure 6:
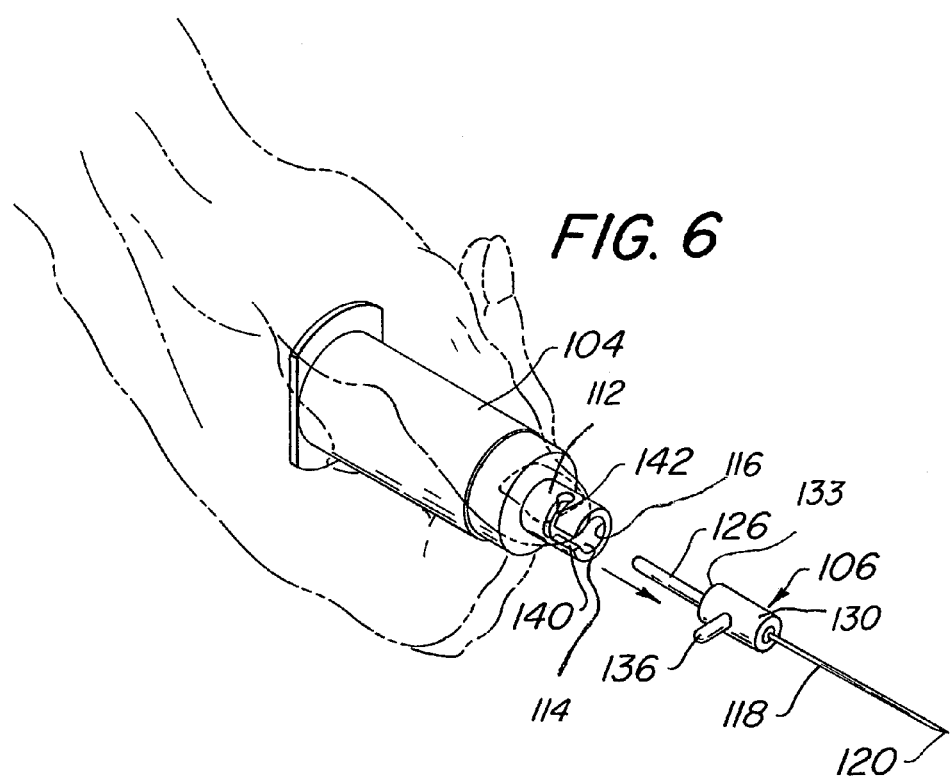

With reference to FIGS. 5 and 6, use of the present embodiment for collecting blood from a patient is now described. While FIG. 6 illustrates removal of the needle assembly, it will be referred to for describing the insertion process as well. The needle assembly 106, separated from the device body 104, is held by the technician who preferably grasps the forward needle cap 122 attached over the front needle end 120. A rear protective cap (not shown) over the second sharp end 124 and sheath 1 26 is then removed. Next, the needle assembly insertion member 130 is inserted the receiver member 112 by moving the rear end 133 of the insertion member 130 rearwardly through the opening 116, the knob 136 being slid through the slot opening 141 into the axial slot section 140 where it loosely fits therein. With the technicians thumb preferably on the knob 136, the needle assembly 106 is then rotated through the radial slot section 142, where it is a fits tightly to secure the needle assembly 106 to the body 102, and into the locking section 144 where the slot of the engagement area just fits the diameter of the knob 136, snap fitting the needle assembly 106 in place. The needle assembly 106 is securely held in place for use. In this case, the needle 118 is inserted into the vein of a patient, and a Vacutainer™ is inserted into the opening 110 onto the second needle end 124 for drawing blood. Once the desired amount of blood is drawn, the technician removes the Vacutainer™, and with his or her thumb preferably on the knob, withdraws the needle 118 from the patient.

Disposal of the needle assembly 106 is now described with reference to FIGS. 5 and 6. Preferably, the needle assembly is disposed of safely in a sharps container for such hazardous waste. With the technician's thumb preferably still on the knob 136, and with the device 102 held vertically over the sharps container with the needle end 120 down, the knob 136 is pushed out of the locking section 144 into the radial section 142 of the slot 138. Once the knob 136 reaches the axial slot section 140, in which the knob 136 loosely fits, the needle assembly 106 separates by moving forwardly from the body 104 and drops into the sharps container after the technician removes his or her thumb. Needle assembly 106 removal and disposal is believed to take no more than about one second. The device body 104 can then be reused with another needle assembly 106 if desired. As shown in FIGS. 5 and 6, the technician's hand is well in back of the needle point from the time he or she withdraws it from the patient until the needle is in the sharps container, preventing accidental sticks and accidental reuse of the needle.

It is noted that the slot 138 described above with reference to FIGS. 1–6 is not limited to being generally L-shaped and in other implementations may come in various configurations.

Exemplary Syringe

The present invention can also be applied to hypodermic syringes. For example, FIGS. 7 and 8 show a perspective view of a needle apparatus 102 in the form of an exemplary syringe 200, which includes a device (syringe) body 204, a needle assembly 206, a needle cap or cover 228, and a novel quick/safe release mechanism 234. Many of components of the syringe 200 are not shown as they are well known and understood by those of ordinary skill in the art. For orientation purposes, similar to the fluid collector described above, and with reference to FIGS. 7 and 8, the left hand side (the needle side) is the front or forward side of the device 102, and the right hand side (body side) is the back or rearward side of the device 102. This orientation shall also apply to the various elements of the device.

In the present embodiment, the syringe body 204 is configured to hold the needle assembly 206 for fluid dispensing. In the illustrated embodiment, the syringe body 204 includes a tube 208 having a plunger 210 slideable therein for dispensing fluid held within the tube 208 as is known in the art. The tube 208 is preferably integrally formed as part of the syringe body 204. The syringe body 204 includes a needle receiver member 212 having a hollow internal portion 214 defining an opening 216 configured to receive the needle assembly 206 therein. The receiver member 212 is preferably cylindrical in shape with the opening 216 generally slightly larger than and configured to receive a portion of the needle assembly 206. Within the opening 216 is a male projection 250 having an opening 252 connected through a channel 253 to the tube 208 in which the fluid travels between the tube 208 and the needle 218. The projection 250 is preferably symmetrical around its axis and tapered to form a mating surface 254 as shown.

The needle assembly 206 preferably includes the longitudinally extending needle 218 having a sharp end 220 for insertion into a patient. A removable safety cap 222 is installed over the end 220 to protect against accidental punctures. The needle assembly 206 preferably also includes a second end 224 that is open for the transfer of fluid between it and the port opening 252.

With further reference to FIG. 8, the needle assembly 206 includes an insert member 230 that supports and is preferably connected to the needle 218, and which is configured to be inserted into the receiver member 212 of the syringe body 204. In the present embodiment, the insert member 230 is preferably cylindrical, formed as a collar 231 as shown which is fastened to the needle 218, and preferably is coaxial to the needle 218. At least a portion of an exterior surface 232 of the collar 231 (insert member 230) fits within the receiver member 212. The insertion end of the insertion member 230 preferably has a female projection 260 that cooperates with the male projection 250 to form a tight seal. The female projection 260 is preferably symmetrical around its axis and is tapered to form a mating surface that cooperates with the mating surface 254. It is seen that as the needle assembly moves to the right in FIG. 8, the seal between the needle assembly 106 and the body 102 gets tighter.

The novel quick/safe release mechanism 234 of the present embodiment is now described in more detail. With further reference to FIGS. 9 and 10, the novel quick/safe release mechanism 234 preferably has two primary elements, a knob 236 and a slot 238. In the preferred embodiment, the knob 236 is formed integrally as part of the needle assembly 206. The slot 238 is preferably formed as part of the syringe body 204. The knob 236 fits within the slot 238 with clearance when the needle assembly 206 is inserted inside the syringe body 204. The combination of the knob 236 and the slot 238 enable the device body 104 and needle assembly 206 to attach and release from each other.

As with the previously described embodiment, the knob 236 is preferably a cylindrically shaped male member in the form of a post that projects from exterior surface 232 of the insert member 230. The knob 236 is preferably perpendicular to the insert member 230 and needle 218, and preferably integral with the insert member 230 or attached to the insert member 230 by any suitable fastening or coupling techniques.

FIG. 10 illustrates a planar view of the slot 238 which is configured to receive the knob 236 when the needle assembly 206 is inserted inside the syringe body 204. Here again, the slot 238 is preferably a generally L-shaped channel located in the receiving member 212. It has a slot opening 241 in the front end 245 of the receiver member 212 and includes a first or longitudinal/axial section 240, and a second or radial section 242.

The axial section 240 is substantially "axial," as discussed above with reference to the fluid collection device and is generally wider than the diameter width of the knob 236 to allow easy insertion and movement of the knob 236 in the slot 238 when inserting the needle assembly 206 into the syringe body 204, or when removing the knob 236 from the slot 238 (and hence separating the needle assembly 206 from the body 204) upon completion of blood/fluid collection.

Located at a pivot angle from axial section 240 is the radial section 242, which is substantially "radial" as previously described. Here, the horizontal radial section 242 is preferably not perfectly radial relative to the axial section, but is angled, preferably 3 to 7 degrees from a perfect axial line 243, away from the needle assembly 206 as shown in FIG. 7. As further described below, this draws the needle assembly 206 into syringe body 204 to form a leak tight seal between the two.

With reference to FIGS. 7, 8, 9 and 10, use of the present embodiment for injecting a fluid into a patient is now described. First, the needle assembly 206 must be attached to the syringe body 204. The needle assembly insertion member 230 is inserted into the receiver member 212, the knob 236 being slid into the axial slot section 240 where it fits loosely therein. With the technician's thumb preferably pushing on the knob 236, the needle assembly 206 is then rotated into the radial slot section 242 until it stops. It is essential that there be no air or liquid leakage between the syringe body 204 and needle assembly 206. This is preferably ensured by applying a slight pressure, (about 3 ounces of pressure) on the knob 236 with the thumb when rotating the knob 236. The knob 236 need not be rotated to the end of the radial slot 242, but is rotated until it stops, i.e., until the needle assembly 206 is abutting the syringe body 204 and cannot be moved inward any further. It is seen that during the rotation of the knob in the radial section 242, the respective mating surfaces 254, 262 of the male projection 250 and female projection 260 are forced closer to one another to form a good seal between the two. It is further seen that the force between the two mating surfaces 254, 262 also pushes the knob 236 tight against the side edge 268 of the radial slot section 242, securely maintaining the knob 238 and thus the needle assembly 206 in place.

Any method of securing the needle cover 222 to the needle assembly 206 should allow a space 270 between the cover 222 and the syringe body 204 as shown to allow for movement of the needle assembly 206 towards the body 204 during the connection process without loosening the cover 222.

Operation of the syringe next involves removal of the needle cover 222, injecting the fluid into the patient, and then withdrawing the needle from the patient and disposing of it in a safe manner. After the needle is removed from the patient, the technician, using one hand only, and preferably holding the syringe over a sharps container, applies thumb pressure to the knob 236 to move it in the radial slot section 242 back towards the axial slot section 240. When the knob reaches the axial slot section 240, the needle assembly drops by gravity into the sharps container. There is no possible contact between the technician and the used needle.

It is noted that the slot 238 described above with reference to FIGS. 7–10 is not limited to being generally L-shaped and in other embodiments may come in various configurations.

It is seen that the present invention provides a safe and cost effective device for eliminating the risk of accidental sticks. Manufacturing costs are reduced since there is no need to provide separate caps or covers for used needles. The slot and the knob can be molded as part of the other components.

Since disposal of just the needle and its holder is made easy, a small sharps container can be located bed-side, reducing the exposure time of a used needle and eliminating the transportation to a wall mounted sharps container.

The invention also affords cost reductions to the user (hospitals, doctor's offices, etc.). Since only the needle and the holder are discarded, many more needles can fit in a sharps container than if the entire syringe body were discarded. This reduces the cost of the sharps container and its subsequent destruction per syringe use.

FIGS. 5 and 6 illustrate a safety feature of this invention. The position of the thumb on the knob prevents the technician's fingers from accidentally contacting the sharp end of a needle which may be contaminated.

Although the invention has been described in language specific to structural features, it is to be understood that the invention defined in the appended claims is not necessarily limited to the specific features or acts described. Rather, the specific features and acts are disclosed as exemplary forms of implementing the claimed invention.

What is claimed is:

1. A needle apparatus capable of collecting or dispensing fluid through a needle, comprising:

a needle assembly having a front and a rear, said needle assembly including an insertion member and a knob projecting from said needle assembly, said needle being supported on and extending in a frontward direction from said insertion member and having a sharp end at the front of said needle assembly for insertion into a patient; and a device body for holding the fluid and which has a front and a rear, said device body including a receiver member disposed at the front of said device body, said receiver member having an internal portion which has an internal portion opening at a front of said receiver member facing frontwardly, said internal portion being configured to receive therein through said opening at least a rear of said insertion member upon movement of said insertion member rearwardly through said opening into said receiver member for releasably attaching said needle assembly to said device body such that said needle extends in said frontward direction away from said body, said device body further having a slot configured to receive said knob when said insertion member is inserted within said receiver member, said knob being configured to be slideable within at least a portion of said slot by a person using said apparatus for attaching said needle assembly to said device body by moving said rear of said insertion member in a rearward direction into said internal portion and for separating said needle assembly from said device body by moving said insertion member in a frontward direction out of said internal portion.

2. The apparatus of claim 1, wherein said slot has a first slot section, and a second slot section at an angle with respect to said first slot section, said knob being slidable from said first slot section into said second slot section for securely holding said needle assembly to said device body, and said knob being slidable out of said second slot section into said first slot section for separating said needle assembly from said device body.

3. The apparatus of claim 2, wherein said first slot section extends substantially longitudinally relative to said apparatus, and said second slot section extends substantially radially relative to said apparatus.

4. The apparatus of claim 3, wherein said slot further includes a locking section.

5. The apparatus of claim 3, wherein said first and second slot sections are sized so that said knob can fit loosely in said slot sections.

6. The apparatus of claim 1, wherein said body is configured to receive a container having a vacuum within, and said needle assembly further includes a second sharp end opposite said first sharp end for insertion into said container.

7. The apparatus of claim 1, wherein said body is configured as a syringe body, and said rear side of said insertion member has an opening for fluid transfer between said needle and said body when said needle assembly is attached to said body.

8. The apparatus of claim 1, wherein said knob projects from and is integrally attached to said insertion member.

9. A needle apparatus capable of collecting or dispensing fluid, comprising:

a needle assembly having a front and a rear, said needle assembly having an insertion member forming a needle holder, a knob projecting from said insertion member, and a needle extending in a frontward direction from said insertion member and having a front end for insertion into a patient; and a device body for holding the fluid and to which said needle assembly is releasably attachable, said body having a front and a rear, said body further comprising a receiver member disposed on the front of said body and having a front end, said receiver member having an internal portion configured to receive said insertion member therein for attaching said needle assembly to said device body, and said internal portion having an opening at the front of said receiver member facing frontwardly which is sized so that the rear of said insertion member can pass there through when moving rearwardly into said internal portion, said receiver member further having a slot and a slot opening in said front end of said receiver member, said slot being configured to receive said knob through said slot opening when said needle assembly is inserted in a rearward direction into said receiver member;

wherein said needle assembly is attachable to said device body by moving said insertion member rearwardly through said internal portion opening into said internal portion thereby moving said knob rearwardly through said slot opening into said slot, and said needle assembly is separable from said device body by moving said knob forwardly out of said slot through said slot opening thereby moving said insertion member forwardly out of said internal portion through said internal portion opening.

10. The apparatus of claim 9 comprising first and second slot sections, wherein said first slot section extends substantially axially relative to said apparatus, and said second slot section extends substantially radially relative to said apparatus, said first slot section being wider than said knob so that said knob fits loosely therein.

11. The apparatus of claim 10, wherein said second slot section has a width so that said knob fits loosely therein.

12. The apparatus of claim 10, wherein said second slot section has a width so that said knob fits tightly therein.

13. The apparatus of claim 11, wherein said second slot is at an angle relative to said first slot within a range of about 3 to about 7 degrees from a line transverse to said first slot section.

14. The apparatus of claim 9, wherein said insertion member includes a female projection having a mating surface, and said body has a male projection having a mating surface which cooperates with said mating surface of said insertion member to form a seal between the two when mated.

15. The apparatus of claim 9, wherein the body forms a syringe for dispensing fluid to a patient, and said insertion member and said body form a leak-proof seal between them when attached to one another so that fluid can move between said device body and said needle assembly.

16. The apparatus of claim 9, wherein the apparatus is a fluid collection device for withdrawing fluid from a patient, said needle having a rear end opposite said front end which extends rearward from said insertion member.

17. The apparatus of claim 1, wherein said slot comprises a first slot section and a second slot section that extends in a direction different from that of said first slot section, said knob being moveable from said first slot section to said second slot section for securely holding said needle assembly to said device body, and said knob being moveable out of said second slot section into said first slot section for separating said needle assembly from said device body.

18. The apparatus of claim 17 wherein said knob fits loosely in said first slot section and snugly in said second slot section.

19. A needle apparatus for collecting or dispensing fluids through a needle and from which the needle can be separated in order to be discarded; said apparatus comprising:

a separable needle assembly having a front and a rear, said needle assembly includes an insertion member and the needle which extends in a frontward direction relative to said insertion member, said insertion member having a front and a rear, said needle having a sharp front end for insertion into a patient, and said needle assembly further including a knob attached to and extending from said needle assembly ;and a device body for holding the fluid and which has a front to which said needle assembly is releasably attachable and a rear opposite said front said device body further having a receiver member disposed at said front of said body and which has a frontwardly facing opening at a front of said receiver member, said receiver member being configured to engageably receive said rear of said insertion member through said receiver member opening when said needle assembly is moved rearwardly into said opening to be attached to said device body, said body further having a slot and a slot opening in a front end of said receiver which slot opening faces frontwardly, said slot being configured to receive said knob through said slot opening when said insertion member is moved rearwardly into said receiver member, said knob being moveable within said slot to attach said needle assembly to said device body when moving said rear of said insertion member in a reward direction into said receiver member, and said knob being moveable frontwardly out of said slot through said slot opening to separate said needle assembly from said device body by moving said insertion member in a frontward direction away from said receiver member and thereby allow said needle assembly to be discarded.

20. The apparatus of claim 19 wherein said slot includes a first slot section and a second slot section, said knob being moveable into said second slot section for holding said needle assembly in its attached position to said device body, and moveable out of said second slot section to release said needle assembly for separation from said device body.

21. A method of using the apparatus of claim 19, comprising:
  (a) holding said apparatus such that the user's thumb is positioned to move said knob when said needle assembly is attached to said device body;
  (b) moving said apparatus to insert said needle into a patient;
  (c) moving said apparatus to withdraw said needle from a patient; and
  (d) moving said knob relative to said device body to separate said needle assembly from said body and discarding said needle directly into a container for disposal.

* * * * *